United States Patent [19]

Skraba

[11] 4,384,160
[45] May 17, 1983

[54] PREQUENCH OF CRACKED STREAM TO AVOID DEPOSITS IN DOWNSTREAM HEAT EXCHANGERS

[75] Inventor: Frank Skraba, Sweeny, Tex.

[73] Assignee: Phillips Petroleum Company, Bartlesville, Okla.

[21] Appl. No.: 199,129

[22] Filed: Oct. 22, 1980

[51] Int. Cl.³ .............................................. C07C 4/02
[52] U.S. Cl. .................................. 585/650; 208/48 Q
[58] Field of Search ...................... 585/650; 208/48 Q

[56] References Cited

U.S. PATENT DOCUMENTS

| | | | |
|---|---|---|---|
| 2,956,093 | 10/1960 | Nicolai | 260/683 |
| 3,174,924 | 3/1965 | Clark et al. | 208/48 Q |
| 3,788,281 | 1/1974 | Campagne | 122/7 R |
| 4,097,544 | 6/1978 | Hengstebeck | 208/48 Q X |
| 4,151,217 | 4/1979 | Amano et al. | 208/48 Q X |
| 4,264,432 | 4/1981 | Gartside | 208/48 R |
| 4,279,734 | 7/1981 | Gwyn | 208/48 Q |

Primary Examiner—Paul F. Shaver

[57] ABSTRACT

Prequenching a conversion zone effluent by direct introduction and heat exchange with a convertable material. The thus quenched effluent passes through a transfer line heat exchange zone with considerably lessened deposition of carbonaceous materials. In one embodiment, liquid ethane and/or propane is injected with the use of a nozzle into the effluent of an ethylene production.

8 Claims, 1 Drawing Figure

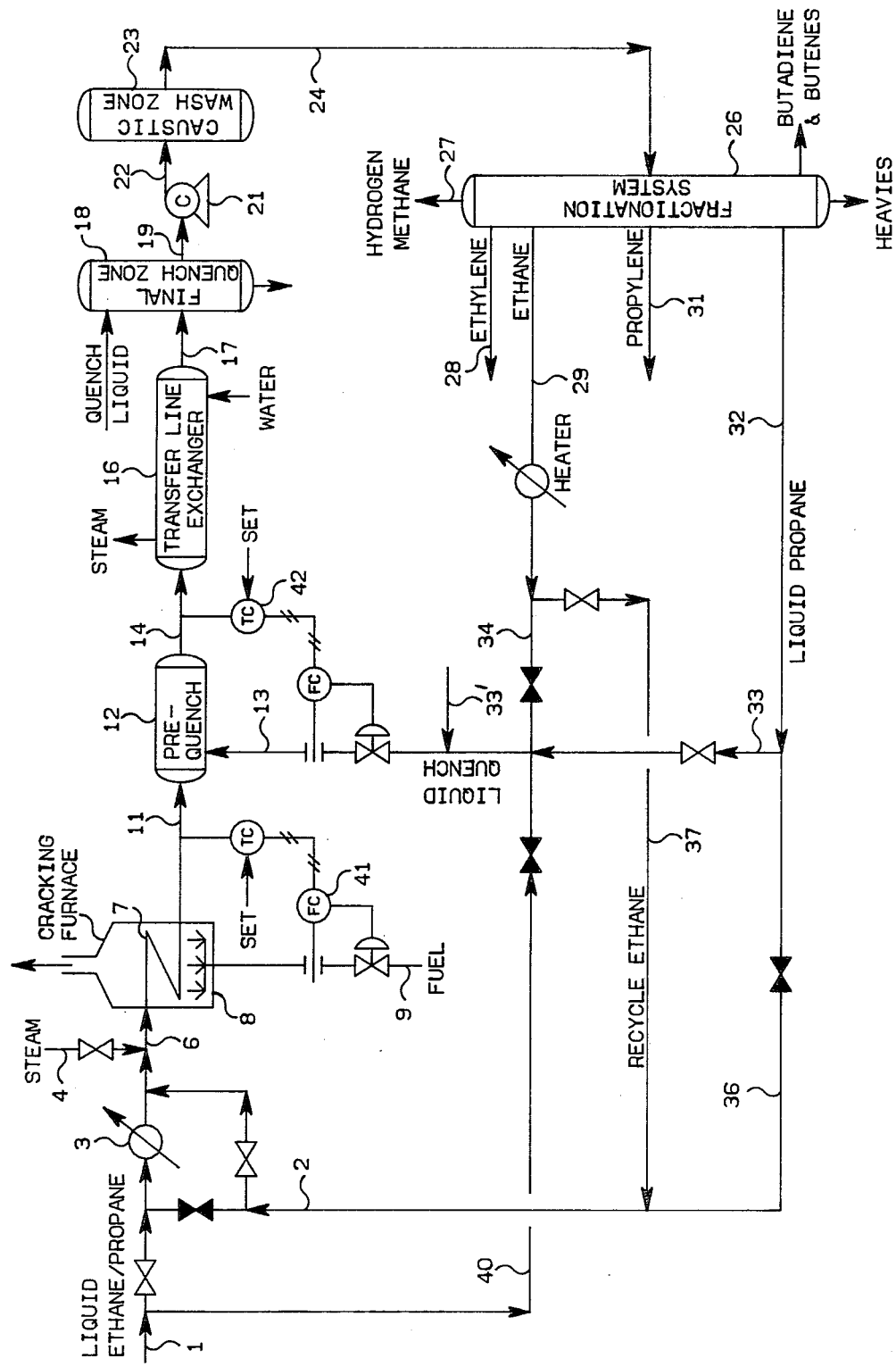

PREQUENCH OF CRACKED STREAM TO AVOID DEPOSITS IN DOWNSTREAM HEAT EXCHANGERS

BRIEF DESCRIPTION OF INVENTION

In a hydrocarbon conversion effected at high temperatures, e.g., of the order of about 1500°-1600° F., converted hydrocarbon is heat exchanged in a so-called transfer line exchanger to recover heat therefrom following which the now somewhat cooled converted hydrocarbon stream is further processed. In an embodiment of the invention, propane which may be in admixture with ethane is cracked to produce a stream of product including ethylene and propylene. The cracked stream is passed through a prequench zone where it is prequenched prior to being passed to a transfer line exchanger thus to avoid deposition of carbonaceous materials in the exchanger. Various materials can be used in the prequench zone. A now preferred prequench material is liquid propane. During the prequenching additional products of conversion are obtained by conversion of the liquid propane.

DETAILED DESCRIPTION

This invention relates to the conversion of hydrocarbons. It also relates to the production of hydrocarbon conversion products. In one of its aspects, the invention relates to an improved process for converting hydrocarbons from which heat is to be recovered as in a transfer line exchanger. In another of its aspects the invention relates to an improved method for avoiding deposition of coke or other hydrocarbonaceous deposits, e.g., polymers, in a transfer line exchanger. In a more specific aspect of the invention, it relates to an improved process for the production of ethylene and propylene from propane which may be in admixture with ethane.

In one of its concepts, the invention provides a process for the conversion of a hydrocarbon at high temperatures of the order of about 1500°-1600° F., or more, wherein prior to extracting heat from a converted hydrocarbon stream, it is prequenched to cool it below a temperature at which there will be formed, otherwise, carbonaceous deposits which in a downstream heat exchanger or in a so-called transfer line exchanger ordinarily used to recover heat as in the production of steam from water. In another of its concepts, the invention provides a process for the cracking or thermal conversion of condensate, a mixture of propane and ethane, to produce a product stream containing ethylene and propylene wherein the product stream prior to being passed through a transfer line exchanger is prequenched with a material which will not produce any substantial adverse effects on later steps in the process, the prequench being practiced prior to passing the converted stream into a transfer line exchanger. In a more specific concept of the invention, it provides a process for the production of ethylene and propylene by cracking a mixture of ethane and propane, as herein described, wherein the prequench liquid will be composed at least in part of propane, the now preferred prequench material.

U.S. Pat. No. 3,174,924, issued Mar. 19, 1965, relates to quenching of hot hydrocarbon fluids from a temperature above carbon-forming temperature to a temperature below said carbon-forming temperature without deposition of carbon in the quench apparatus and in the transfer conduit downstream from the quench apparatus. U.S. Pat. No. 4,097,544, issued June 27, 1978, discloses a system for steam-cracking hydrocarbons and transfer-line exchanger therefor, the system being described to produce ethylene. U.S. Pat. No. 4,151,217, issued Apr. 24, 1979, describes a method for cooling cracked gases of low boiling hydrocarbons and preventing the formation of or accumulation of coke or of other reactants by-products of said olefins produced by the pyrolysis of hydrocarbons by maintaining a proportion extending from the outlet part of the pyrolysis reaction tube to a multitubular quenching device at a temperature below 450° C. The disclosures of the patents are incorporated by this reference to them.

It is an object of this invention to provide an improved process for the production of hydrocarbon conversion products produced at high temperatures of the order of about 1500° to 1600° F. It is another object of the invention to provide a process for the improved production of ethylene and propylene from a low boiling hydrocarbon, e.g., ethane and/or propane. A further object of this invention is to provide an improved process for the production of, say, ethylene and propylene from, say, ethane and/or propane which will reduce the heat requirement and/or increase the yield obtainable from a given heating zone. A further object, still, is to improve an ethylene furnace product quenching zone and/or apparatus. A still further object of the invention is to provide downstream from a cracking furnace, e.g., a furnace in which ethylene is produced, a maximum high temperature heating medium in which to produce steam, as in a transfer line indirect heat exchanger.

Other aspects, concepts, objects and the several advantages of this invention are apparent from a study of this disclosure and the appended claims.

According to the present invention, there is provided a process for conversion of a hydrocarbon at high temperatures, e.g., propane and/or ethane to produce ethylene, wherein a transfer line heat exchange zone is employed to recover heat, as in the production of steam, there being practiced on the conversion product prior to recovery of heat therefrom as in the production of steam, a prequench, employing for said prequench or at least a part thereof, some of the feed to be converted, thus to save energy and to increase the yield of ethylene for a given size conversion zone or apparatus.

DESCRIPTION OF DRAWING

Referring now to the drawing, there is illustrated diagrammatically a conversion of a mixture of ethane and propane to produce hydrogen, methane, ethylene, propylene, butenes, and butadiene, as known in the art.

According to the invention, there is shown a prequench zone or station now further described in connection with the overall embodiment of the invention shown.

According to the invention, the use of at least some propane or other material convertable to the desired product in the prequench zone 12 accomplishes at least two functions. The function to avoid deposition of carbonaceous materials is accomplished along with the function of using the available heat present in the furnace effluent to further convert the quench materials, in which embodiment at least propane, to additional quantities of desired product ethylene.

Liquid propane and/or ethane is fed by 1 with recycle propane and/or ethane from 2 through vaporizer 3.

Steam 4 is added to the vapor from vaporizer 3. The admixture is charged by conduit 6 to cracking coil 7 in furnace 8 to effect conversion of the feed. Fuel 9 is burned to heat the furnace 8 to ethylene production conditions, which are known. The furnace effluent comprising hydrogen, methane, ethylene, ethane, propylene, propane, carbon dioxide, and other materials (acetylenes, etc.) is passed by way of conduit 11 to prequench zone 12 to which liquid propane and/or ethane is charged by conduit 13 to quickly and by direct heat exchange to decrease the temperature of the furnace effluent 11 by about 25° F. to about 200° F. so that coking and deposition is minimized in subsequent equipment.

The temperature is reduced to a level at which carbonaceous materials even if formed will not form deposits in the downstream apparatus. The pequench effluent from 12, comprising additional ethylene produced according to the invention by partial conversion of the liquid prequench 13 in zone 12, is passed by way of conduit 14 to transfer line exchange 16. Since the mass in 14 has been prequenched by at least about 25° F. below that of the conventionally charged furnace effluent 11, the deposition of coke, polymer, and the like, is considerably minimized in this transfer line exchanger 16. By minimizing coking and deposits in transfer line exchanger 16, extended operation can be realized and improved recovery of waste heat is obtained.

From the transfer line exchanger 16 the cooled mass is passed by conduit 17 to final quench 18 and thence by 19 to compressor 21 and 22 to aqueous caustic washer 23 (for $CO_2$ removal). From caustic washer 23 the mass is passed by 24 to fractionation 26.

Fractionation 26 comprises several fractionation sections (demethanizer, ethane-ethylene splitter, propane-propylene splitter, depropanizer, and the like). For simplicity, a single zone 26 has been shown. Methane and hydrogen are recovered at 27; produce ethylene is recovered at 28; unconverted ethane is removed at 29; product propylene is recovered at 31, and unreacted propane at 32.

A portion of the liquid propane 32 is passed by way of 33 and 13 as the liquid propane prequench fluid for prequench zone 12. This prequench liquid propane preferably is injected into the furnace effluent gas by way of a nozzle means to ensure that fine droplets of liquid will be quickly and thoroughly admixed with the hot gas. Any remainder of the propane can be recycled to the cracking zone 7 by way of 36, 2 and 6.

Although not shown, liquid ethane 29 can be used as the prequench liquid and can be passed by 34 and 13 to prequench zone 12. If desired, an admixture of liquid ethane and propane can be charged by 34 and 33, respectively, to 13 as the prequench liquid. That ethane not used as prequench can be passed via 37, 2 and 6 to the cracking coil 7.

If desired, a portion of the liquid feed 1 can be charged by 40 and 13 as the prequench liquid. Any combination of streams 33, 34 and 40 can be used as the prequench liquid. Any desired other conventional or inert quench material can be added alone or with, say, propane at 33'.

A temperature sensing means 41 on the furnace effluent 11 actuates control of flow of fuel to the burners in furnace 8. A thermocouple, a temperature controller, flow controller, orifice means, and control valve means are included.

A temperature sensing means 42 on the prequench effluent 14 actuates control of prequench liquid 13 to prequench zone 12. A thermocouple, a temperature controller, flow controller, orifice means, and control valve means are included. At control means (not illustrated) across the prequench zone (set at about 25° F. to about 200° F.) can be used to control the amount of prequench liquid flowing in conduit 13 to prequench zone 12.

| CALCULATED EXAMPLE | |
|---|---|
| Feed (1) | |
| Methane, lbs/hr | 262 |
| Propane, lbs/hr | 9633 |
| Ethane, lbs/hr | 23985 |
| Total, lbs/hr | 33880 |
| Recycle (2) | |
| Propane, lbs/hr | 0 |
| Ethane, lbs/hr | 17162 |
| Total, lbs/hr | 17172 |
| Steam (4) at 338° F. | |
| pounds/hr | 16218 |
| Furnace Effluent (11) | |
| Temperature, °F. | 1540 |
| Pressure, psig | 8.4 |
| Pounds/hr. (including steam) | 67260 |
| Prequench Propane Liquid (13) | |
| Temperature, °F. | 100 |
| Pressure, psig | 100 |
| Pounds/hr | 5075 (3168 outside $C_3$) via 33' |
| Prequench Effluent (14) | |
| Temperature, °F. | 1440 |
| Pressure, psig | 8.3 |
| Pounds/hr | 72335 |
| Ethylene Produced from Feed (1) and Recycle (2), lbs/hr | 23796 |
| Additional Ethylene Produced by Prequench of Propane Liquid (13) in Zone 12, lbs/hr | 1385 (a) |

(a) Plus:
887 lbs/hr Propylene
75 lbs/hr butadiene
72 lbs/hr butenes

By prequenching the above amount, the on-stream time of the transfer line exchanger between decokings is considerably extended. This increases the stream time of the heater and capacity of the unit. Also, better heat recovery will be achieved in transfer line heat exchanger 16 due to less fouling thereof from coke, and advantageously, more steam will be generated in exchanger 16.

One skilled in the art in possession of this disclosure, having studied the same, will recognize that the specific function of the interpositioned prequench zone 12, as herein described, is an advance in the art not clearly obvious from that art, as exemplified by the patents incorporated herein by reference.

Reasonable variation and modifications are possible within the scope of the foregoing disclosure, the drawing and the appended claims to the invention, the essence of which is that a prequench zone has been provided just ahead of a transfer line heat exchanger as in the production of, say, ethylene and propylene, from propane and/or ethane at high temperatures and that the prequench is so operated as to substantially reduce deposition of carbonaceous materials in the transfer line heat exchanger, yielding increased on stream time between cleaning, and also, advantageously, the conversion of additional feed or other prequench material.

I claim:

1. A process for the cracking of a hydrocarbon stream comprising:
    (a) at least partially cracking a hydrocarbon stream in a heating zone at a temperature at which carbonaceous material will form and deposit downstream,
    (b) passing the at least partially cracked hydrocarbon stream from said heating zone directly to a prequench zone,
    (c) prequenching, in said prequench zone, said at least partially cracked hydrocarbon stream with a prequench stream comprising at least one hydrocarbon that can be cracked in said prequench zone, and
    (d) passing the quenched hydrocarbon stream through a transfer line heat exchange zone to recover usable heat.

2. A process in accordance with claim 1 wherein said prequench stream comprises a portion of said hydrocarbon stream that has been diverted prior to heating in said heating zone.

3. A process in accordance with claim 1 wherein said prequench stream comprises a portion of said quenched hydrocarbon stream that has passed through said transfer line heat exchange zone.

4. A process in accordance with claim 1, 2 or 3 wherein propane is cracked in said heating zone and said prequench stream comprises propane.

5. A process in accordance with claim 4 wherein ethane is also cracked in said heating zone and wherein said prequench stream further comprises ethane.

6. A process in accordance with claim 1 wherein said quenched hydrocarbon stream, after passing through said transfer line heat exchange zone, is fractionated in a fractionation zone.

7. A process in accordance with claim 6 wherein said prequench stream comprises a liquid hydrocarbon from said fractionation zone.

8. A process in accordance with claim 7 wherein said liquid hydrocarbon comprises a member of the group consisting of propane and ethane.

* * * * *